United States Patent
Ieda et al.

(10) Patent No.: US 8,377,275 B2
(45) Date of Patent: Feb. 19, 2013

(54) GAS SENSOR CONTROL DEVICE AND GAS SENSOR CONTROL METHOD

(75) Inventors: Norikazu Ieda, Ichinomiya (JP); Yoshinori Inoue, Aichi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 553 days.

(21) Appl. No.: 12/623,801

(22) Filed: Nov. 23, 2009

(65) Prior Publication Data
US 2010/0133116 A1 Jun. 3, 2010

(30) Foreign Application Priority Data

Nov. 25, 2008 (JP) ................. 2008-299534
Jan. 7, 2009 (JP) ................. 2009-001411

(51) Int. Cl.
*G01N 27/407* (2006.01)
(52) U.S. Cl. .................. 204/426; 205/784.5
(58) Field of Classification Search .............. 204/421, 204/424–429; 205/783.5–785.5
See application file for complete search history.

(56) References Cited

U.S. PATENT DOCUMENTS

| | | | |
|---|---|---|---|
| 6,120,677 A | 9/2000 | Yamada et al. | |
| 6,164,125 A | 12/2000 | Kawase et al. | |
| 7,142,976 B2 | 11/2006 | Inoue et al. | |
| 2005/0288847 A1* | 12/2005 | Inoue et al. | 701/114 |
| 2006/0157348 A1 | 7/2006 | Inoue et al. | |
| 2008/0060941 A1 | 3/2008 | Ieda et al. | |

FOREIGN PATENT DOCUMENTS

| | | |
|---|---|---|
| JP | 3833687 A | 10/2006 |
| JP | 2008-70194 A | 3/2008 |

* cited by examiner

*Primary Examiner* — J. Christopher Ball
(74) *Attorney, Agent, or Firm* — Sughrue Mion, PLLC (57) ABSTRACT

A gas sensor control apparatus 5 is connected to a gas sensor (8) including cells (14, 24) each having a pair of electrodes provided on a solid electrolyte body (13, 23), and includes a sensor drive circuit (52). The gas sensor control apparatus (5) includes an instruction unit for outputting an instruction for setting the sensor drive circuit (52) to a deenergization state so as to stop the supply of electricity to the cells (14, 24) and an instruction for setting the sensor drive circuit (52) to an energization state so as to supply electricity to the cells (14, 24); a setting unit (55) for setting the sensor drive circuit (52) to the deenergization state or the energization state; and a wiring anomaly detection unit (58) for detecting a wiring anomaly of the sensor drive circuit (52) or the gas sensor (8). The gas sensor control apparatus (5) further includes an anomaly final determination unit, operable when a wiring anomaly is detected, for performing return-from-anomaly checking processing so as to cause the instruction unit to output the deenergization instruction and then output the energization instruction.

6 Claims, 5 Drawing Sheets

| ENERGIZATION STATE (OPERATION MODE) | SWITCHES | | | | |
|---|---|---|---|---|---|
| | SW1 | SW2 | SW3 | SW4 | SW5 |
| ENERGIZATION STATE FOR GAS CONCENTRATION MEASUREMENT | OFF | ON | ON | OFF | ON |
| ENERGIZATION STATE FOR SENSOR PROTECTION | OFF | OFF | OFF | OFF | OFF |
| PRE-ACTIVATION ENERGIZATION STATE | ON | OFF | OFF | ON | ON |

GAS SENSOR CONTROL DEVICE AND GAS SENSOR CONTROL METHOD

TECHNICAL FIELD

The present invention relates to a sensor control apparatus and a sensor control method for controlling the energization state of a gas sensor including at least one cell which includes a solid electrolyte body and a pair of electrodes provided on the solid electrolyte body.

BACKGROUND ART

An oxygen sensor, which detects the concentration of oxygen within exhaust gas, is known as a gas sensor used for improving the fuel consumption of an internal combustion engine of an automobile or the like and/or for performing combustion control for the engine. Further, there has been demanded reduction in the amount of nitrogen oxides ($NO_x$) within exhaust gas in order to cope with the strengthened exhaust gas regulation for automobiles, and $NO_x$ sensors which can directly measure $NO_x$ concentration have been developed.

Such a gas sensor includes a gas sensor element having one or more cells each composed of oxygen-ion conductive solid electrolyte layer formed of zirconia or the like, and a pair of electrodes formed on the surface of the solid electrolyte layer. The gas sensor is configured to detect the concentration of a specific gas on the basis of the output from the gas sensor element.

One known example of such a gas sensor is a wide-range air-fuel-ratio sensor (hereinafter may be referred to as a "UEGO sensor"), which is configured such that two cells (an oxygen-concentration detection cell and an oxygen pump cell) are disposed with a measurement chamber disposed therebetween, and a gas to be measured (hereinafter referred to as an "object gas") is introduced into the measurement chamber via a diffusion resistor so as to detect oxygen contained in the object gas. Further, another known example of such a gas sensor is an $NO_x$ gas sensor which includes three cells in total; i.e., the above-described two cells (an oxygen-concentration detection cell and an oxygen pump cell), and a cell for detecting $NO_x$ gas concentration.

A sensor drive circuit is connected to such a gas sensor so as to supply electricity to cells via the sensor drive circuit, and the concentration of a specific gas contained in the object gas is measured on the basis of the output of a cell. A control apparatus, including the sensor drive circuit, is called a "gas sensor control apparatus." Further, there are various states in which electricity is supplied to cells (hereinafter referred to "energization states"), including an energization state for protection which is provided for protecting the gas sensor; a pre-activation energization state in which a minute current is supplied to the gas sensor in an non-activated state; and an energization state for gas concentration measurement which is provided for measurement of the concentration of a specific gas.

Of these energization states, the energization state for protection is established in an operation mode in which the electrical continuity between the cells and the sensor drive circuit is cut off so as to stop the flow of current to the gas sensor, to thereby protect the gas sensor. Further, the pre-activation energization state is established in an operation mode in which a minute current is supplied to the oxygen-concentration detection cell so as to accumulate oxygen of a reference concentration in the reference oxygen chamber of the oxygen-concentration detection cell, to thereby prepare for gas concentration measurement.

Incidentally, the sensor drive circuit or wiring lines (electricity supply lines) of the gas sensor may suffer a wiring anomaly, such as wire breakage or short-circuiting with a battery or the ground. When, irrespective of occurrence of such a wiring anomaly, the energization state for gas concentration measurement is continued so as to measure the concentration of the specific gas, an excessively large current flows through the gas sensor, and the gas sensor may be broken.

In view of the above, there has been developed a technique for cutting off the electrical connection between the sensor drive circuit and the gas sensor upon detection of a wiring anomaly so as to bring the gas sensor into an energization state for protection, and then diagnosing the wiring anomaly so as to determine the details of the anomaly and the location where the anomaly has occurred (see Patent Document 1). This technique prevents an over current from continuously flowing to the gas sensor even after a wiring anomaly has occurred, to thereby prevent breakage of the gas sensor.

Further, when an instruction for switching to the energization state for gas concentration measurement from another energization state is output to the sensor drive circuit without awareness of a wiring anomaly, similarly, an excessively large current flows to the gas sensor, and the gas sensor may be broken.

In view of the above, there has also been developed a technique for permitting the switching to the energization state for gas concentration measurement only when the state immediately before switching is the pre-activation energization state, to thereby allow detection of an anomaly without breaking the gas sensor (see Patent Document 2). If a wiring anomaly occurs in the pre-activation energization state in which a minute current is supplied to the gas sensor, the voltage applied to the gas sensor deviates from a normal range, whereby a wiring anomaly can be detected.

PRIOR ART DOCUMENTS

Patent Documents

[Patent Document 1] Japanese Patent No. 3833687
[Patent Document 2] Japanese Patent Application Laid-Open (kokai) No. 2008-70194

SUMMARY OF THE INVENTION

Problems to be Solved by the Invention

Incidentally, the conventional gas sensor control apparatus is configured such that, even when an anomaly is detected only one time, the gas sensor control apparatus immediately determines that an anomaly has occurred, and stops the operation of the sensor or switches the energization state of the sensor to the energization state for protection. However, the gas sensor control apparatus may erroneously detect an anomaly because of influence of noise or the like, despite the wiring being normal. Further, in the case where a wiring anomaly is detected erroneously, the erroneously detected wiring anomaly may disappear immediately. Therefore, if the operation of the sensor is stopped every time an anomaly is detected, wasteful time is needed for return to gas-concentration-measurement operation. In particular, erroneous detection of a wiring anomaly tends to occur in association with short-circuiting.

Further, in the case where the conventional gas sensor control apparatus is modified so as to check whether or not a wiring anomaly is detected through erroneous detection, a new energization state and an additional circuit must be provided. In such a case, the sensor drive circuit has a problem in that it requires additional circuit components, etc., whereby the size of the circuit increases.

In view of the foregoing, an object of the present invention is to provide a gas sensor control apparatus which can accurately determine whether or not a wiring anomaly has occurred in a sensor drive circuit or a gas sensor, and which does not require wasteful time to return to gas-concentration-measurement operation after the wiring anomaly disappears.

Means for Solving the Problems

In order to achieve the above-described object, the present invention provides a gas sensor control apparatus including a sensor drive circuit which is connected to a gas sensor having at least one cell composed of a solid electrolyte body and a pair of electrodes provided on the solid electrolyte body and which is adapted to supply electricity to the cell in order to drive the gas sensor, the gas sensor control apparatus comprising an instruction unit for selectively outputting a deenergization instruction for setting the sensor drive circuit to a deenergization state for stopping supply of electricity to the cell and an energization instruction for setting the sensor drive circuit to an energization state for supplying electricity to the cell; a setting unit, operable upon receipt of each of the instructions, for setting the sensor drive circuit to the deenergization state or the energization state in accordance with the received instruction; a wiring anomaly detection unit for detecting a wiring anomaly of the sensor drive circuit or the gas sensor; a determination unit, operable when the wiring anomaly detection unit detects the wiring anomaly, for performing return-from-anomaly checking processing so as to instruct the instruction means to output the deenergization instruction for setting the sensor drive circuit to the deenergization state and then output the energization instruction for setting the sensor drive circuit to the energization state, and for performing determination processing so as to determine whether or not the wiring anomaly has disappeared as a result of performance of the return-from-anomaly checking processing; and an anomaly final determination unit for finally determining, on the basis of the result of the determination processing, whether or not the wiring anomaly has occurred.

The gas sensor control apparatus having the above-described configuration operates as follows. Even when the gas sensor control apparatus detects a wiring anomaly once, the sensor control apparatus does not immediately stop the operation of the gas sensor by finally determining that the wiring anomaly has occurred. Instead, the gas sensor control apparatus causes the sensor drive circuit to return to the energization state and then again determines whether or not the wiring anomaly is present. Thus, it becomes possible to prevent erroneous detection of a wiring anomaly and prevent the operation of the gas sensor from being stopped meaninglessly when the wiring anomaly disappears immediately.

The gas sensor control apparatus is preferably configured such that, when the determination processing determines that the wiring anomaly has not yet disappeared, the anomaly final determination unit causes the determination unit to repeat the return-from-anomaly checking processing at least one more time, and finally determines that the wiring anomaly has occurred, when the wiring anomaly does not disappear even after the return-from-anomaly checking processing is performed a predetermined number of times equal to or greater than two times.

According to the above-described configuration, the return-from-anomaly checking processing is performed at least two times. Therefore, the possibility of the dissolution of an incidental wiring anomaly or erroneous detection of a wiring anomaly increases further, and there can be suppressed occurrence of a state where the operation of the sensor is stopped every time a wiring anomaly is detected, which results in necessity of wasteful time for resuming the gas-concentration-measurement operation.

Preferably, the above-described gas sensor control apparatus comprises a heater control circuit for controlling a heater provided on the gas sensor so as to heat the cell to an activation temperature or higher, wherein the heater control circuit energizes the heater at an intermediate voltage which is lower than a maximum voltage but not lower than a voltage at which the heater can maintain the activation temperature of the cell, during a period between a point in time at which the wiring anomaly detection unit first detects the wiring anomaly and a point in time at which the anomaly final determination unit finally determines whether or not the wiring anomaly has occurred.

According to this configuration, during a period between a point in time at which a wiring anomaly is first detected and a point in time at which the final determination is made as to whether the wiring anomaly has occurred, the heater is suitably energized at an intermediate voltage by use of the heater control circuit, which energizes and controls the heater for heating the cell to the activation temperature or higher. Therefore, in the case where the gas sensor stops the ordinary operation (the gas-concentration-measurement operation) upon detection of a temporary wiring anomaly and then resumes the ordinary operation (the gas-concentration-measurement operation) because of the final determination that a wiring anomaly has not occurred, the gas sensor can be prevented from cooling down. Therefore, the sensor can quickly resume the ordinary operation. Meanwhile, in some cases, a detected wiring anomaly is finally determined to have occurred. If the heater is energized at the maximum voltage in such a case, electrical power is uselessly consumed. However, in the present invention, since the heater is energized at an intermediate voltage, the power consumption can be reduced.

Preferably, the above-described gas sensor control apparatus is configured such that the heater control circuit deenergizes the heater when the anomaly final determination unit finally determines that the wiring anomaly has occurred.

According to this configuration, the heater is deenergized after the anomaly is finally determined to have occurred (hereinafter referred to as "anomaly final determination"). Therefore, it is possible to prevent breakage of the gas sensor due to an excessive temperature increase, which would otherwise occur when heating of the cells (gas sensor) by the heater is continued after the anomaly final determination, and to suppress useless consumption of electrical power.

In order to achieve the above-described object, the present invention provides a method of controlling a gas sensor control apparatus including a sensor drive circuit which is connected to a gas sensor having at least one cell composed of a solid electrolyte body and a pair of electrodes provided on the solid electrolyte body and which is adapted to supply electricity to the cell in order to drive the gas sensor, wherein the sensor drive circuit is configured such that, in response to an externally applied deenergization instruction, the sensor drive circuit enters a deenergization state for stopping supply of electricity to the cell and, in response to an externally applied energization instruction, the sensor drive circuit enters an energization state for supplying electricity to the cell, the method comprising:

a wiring anomaly detection step of detecting a wiring anomaly of the sensor drive circuit or the gas sensor;

a determination step of performing, when the wiring anomaly is detected, return-from-anomaly checking processing so as to output to the sensor drive circuit the deenergization instruction for setting the sensor drive circuit to the deenergization state and then output to the sensor drive circuit the energization instruction for setting the sensor drive circuit to the energization state, and performing determination processing so as to determine whether or not the wiring anomaly has disappeared as a result of performance of the return-from-anomaly checking processing; and an anomaly final determination step of finally determining, on the basis of the result of the determination processing, whether or not the wiring anomaly has occurred.

The above-described gas sensor control method is preferably such that, when the determination processing determines that the wiring anomaly has not yet disappeared, the anomaly final determination step causes the return-from-anomaly checking processing of the determination step to be repeated at least one more time, and finally determines that the wiring anomaly has occurred, when the wiring anomaly does not disappear even after the return-from-anomaly checking processing is performed a predetermined number of times equal to or greater than two times.

The above-described gas sensor control method is preferably such that the above-described gas sensor control apparatus comprises a heater control circuit for controlling a heater provided on the gas sensor so as to heat the cell to an activation temperature or higher, wherein the method further comprises a step of controlling the heater control circuit such that the heater control circuit energizes the heater at an intermediate voltage which is lower than a maximum voltage but not lower than a voltage at which the heater can maintain the activation temperature of the cell, during a period between a point in time at which the wiring anomaly detection step first detects the wiring anomaly and a point in time at which the anomaly final determination step finally determines whether or not the wiring anomaly has occurred.

Preferably, the above-described gas sensor control method further comprises a step of controlling the heater control circuit such that the heater control circuit deenergizes the heater when the anomaly final determination step finally determines that the wiring anomaly has occurred.

The gas sensor control method can provide actions and effects similar to those provided by the above-described gas sensor control apparatus.

MODE FOR CARRYING OUT THE INVENTION

Embodiments of the present invention will now be described.

A. First Embodiment

Figure 1:
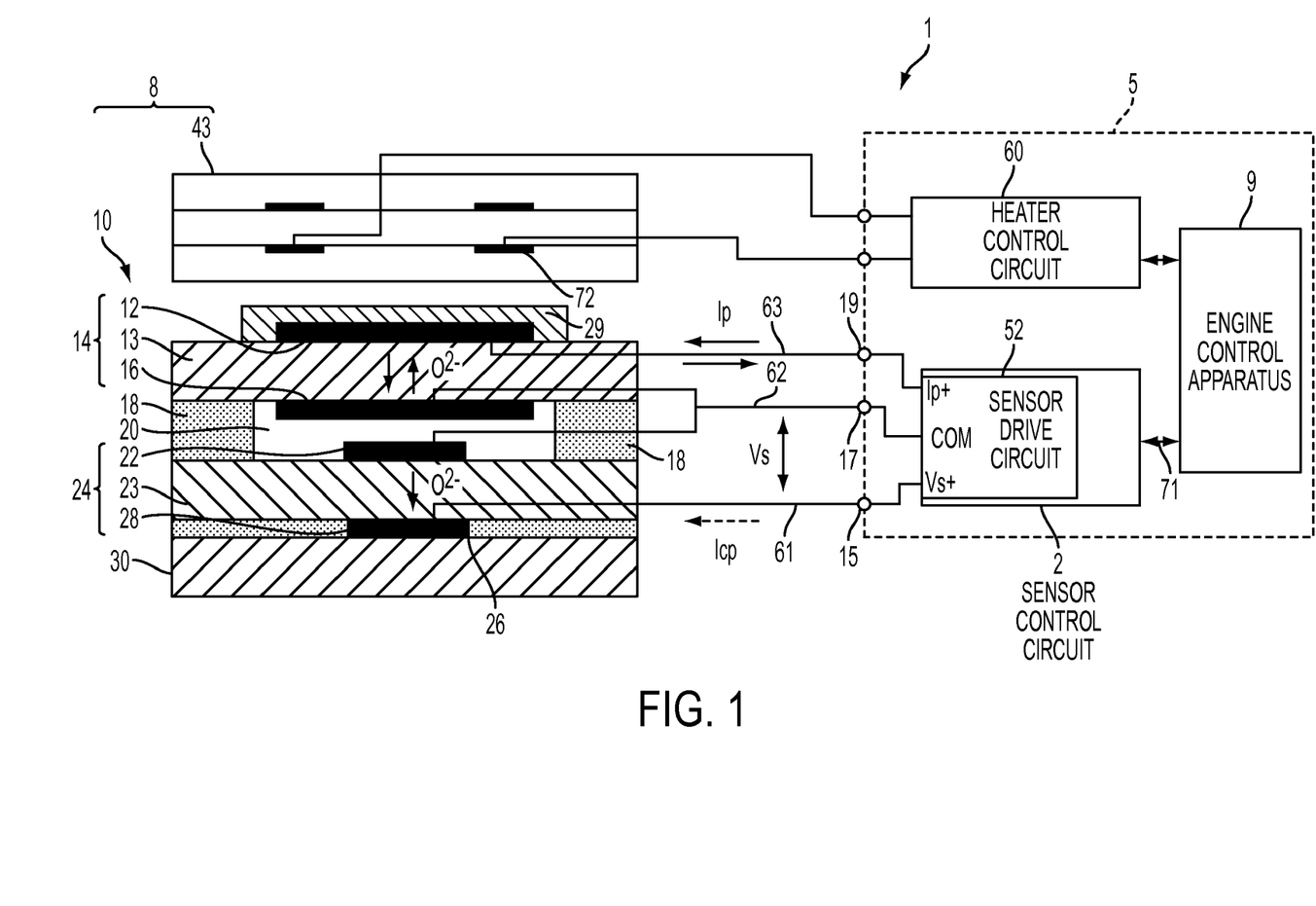
FIG. 1 Schematic diagram of an internal-combustion-engine control system including an electronic control unit.

FIG. 1 is a schematic diagram showing the configuration of an internal-combustion-engine control system 1 which includes a gas sensor control apparatus (electronic control unit; ECU) 5 according to an embodiment of the present invention. Notably, the internal-combustion-engine control system 1 executes various control processings for controlling the operation state of the internal combustion engine (engine), and also executes processing for detecting the concentration of a specific gas (oxygen) contained in an object gas (exhaust gas).

The internal-combustion-engine control system 1 includes an electronic control unit 5 and a gas sensor 8, which is attached to an exhaust pipe of the engine. The electronic control unit 5 includes a sensor control circuit 2 which controls the gas sensor 8 (a sensor element 10), an engine control apparatus 9 (hereinafter, also referred to as the "engine CPU" 9), and a heater control circuit 60 which controls a heater 43. The sensor control circuit 2 includes a sensor drive circuit 52. The engine control apparatus 9 is connected to the heater control circuit 60, and controls the heater control circuit 60 such that the temperature of the sensor element 10 is maintained at an operation temperature (hereinafter, also referred to as an activation temperature; e.g., 550 to 900° C.). The engine control apparatus 9 is also connected to the sensor control circuit 2 via a transmission cable 71, and controls the sensor control circuit 2.

The gas sensor 8 includes the sensor element 10 which detects the concentration of oxygen contained in the object gas (exhaust gas) in a wide range and the heater 43 which maintains the sensor element 10 at the operation temperature, and operates as a so-called wide-range air-fuel-ratio sensor. Further, the sensor element 10 includes an oxygen pump cell 14, a porous diffusion layer 18, an oxygen-concentration detection cell 24, and a reinforcing plate 30. The specific structure of the gas sensor 8 will be described later.

The sensor control circuit 2 includes, among others, the sensor drive circuit 52 electrically connected to the gas sensor 8. The sensor drive circuit 52 supplies electricity to the gas sensor 8 (the oxygen pump cell 14 and the oxygen-concentration detection cell 24), drives and controls these cells, and detects the output (a gas detection signal) of the oxygen pump cell 14 and an element impedance (in actuality, an impedance signal Vrpvs, which changes in accordance with the element impedance of the oxygen-concentration detection cell 24). The sensor control circuit 2 outputs the detected gas detection signal and an element resistance signal (impedance signal) to the engine control apparatus 9.

Notably, the sensor control circuit 2 can be realized in the form of, for example, an ASIC (application-specific integrated circuit). The gas detection signal changes in accordance with the oxygen concentration in the object gas, and is used for measurement of the oxygen concentration. The element impedance (the impedance signal) represents the internal resistance of the gas sensor 8, and changes with the temperature of the gas sensor 8 in accordance with a correlation therebetween. Since detection of the element impedance and calculation of the temperature of the gas sensor 8 can be performed by use of know methods, their detailed descriptions will not be provided here.

The sensor control circuit 2 (the sensor drive circuit 52) has a Vs+ terminal, a COM terminal, and an Ip+ terminal, which are electrically connected to a first connection terminal 15, a second connection terminal 17, and a third connection terminal 19, respectively, of the electronic control unit 5. A second detection electrode 28 of the sensor element 10, which will be described later, is electrically connected to the Vs+ terminal of the sensor control circuit 2 via the first connection terminal 15 and a wiring line 61. Further, a first detection electrode 22 and a second pump electrode 16 of the sensor element 10 are electrically connected to the COM terminal of the sensor control circuit 2 via the second connection terminal 17 and a wiring line 62. Similarly, a first pump electrode 12 of the sensor element 10 is electrically connected to the Ip+ terminal of the sensor control circuit 2 via the third connection terminal 19 and a wiring line 63. The sensor drive circuit 52 is electrically connected to the gas sensor 8 in this manner, and detects the gas detection signal and the element resistance signal.

A control section 55 can be composed of a logic circuit which executes various kinds of control processings in the sensor control circuit 2.

The engine control apparatus 9 may be a microcomputer which includes a CPU (central processing unit), a storage section (RAM and ROM) for storing data, programs, etc., and input and output ports for receiving signals from external equipment and for outputting signals to the external equipment. In the engine control apparatus 9, in accordance with programs stored in the storage section, the CPU executes various kinds of computation processings, and controls execution of instructions for computation, data transfer, etc. In the engine control apparatus 9, signals input to the input port are reflected on the contents of an input port register, and the contents of an output port register are output to the output port as signals.

The engine control apparatus 9 computes the oxygen concentration on the basis of the gas detection signal Vip output from the sensor control circuit 2. The engine control apparatus 9 executes combustion control (air-fuel-ratio control), etc. for the engine by use of the oxygen concentration obtained from the computation, to thereby control the operation state of the internal combustion engine.

Further, the engine control apparatus 9 also executes anomaly final determination processing and instruction output processing for outputting to the sensor control circuit 2 instructions for switching the energization state to be described later (hereinafter may be referred as "switching instructions"). Notably, the above-mentioned instructions (switching instructions) correspond to the "instructions" in the claims. Also, the engine control apparatus 9 corresponds to the "instruction unit" in the claims.

Next, the structure of the gas sensor 8 will be described.

The oxygen pump cell 14 includes oxygen-ion-conductive solid electrolyte body 13, which is formed into a plate-like shape from partially stabilized zirconia. First and second pump electrodes 12 and 16 mainly formed of platinum are formed on the front and back surfaces of the solid electrolyte body 13. The first pump electrode 12 is electrically connected to the third connection terminal 19 of the electronic control unit 5 via the wiring line 63, and the second pump electrode 16 is electrically connected to the second connection terminal 17 of the electronic control unit 5 via the wiring line 62. Notably, the first pump electrode 12 is covered with a porous protection layer 29, and is protected from poisoning substances, etc. by the porous protection layer 29.

The oxygen-concentration detection cell 24 includes oxygen-ion-conductive solid electrolyte body 23, which is formed into a plate-like shape from partially stabilized zirconia. First and second detection electrodes 22 and 28 mainly formed of platinum are formed on the front and back surfaces of the solid electrolyte body 23. The first detection electrode 22 is electrically connected to the second connection terminal 17 of the electronic control unit 5 via the wiring line 62, and is also electrically connected to the second pump electrode 16. The second detection electrode 28 is electrically connected to the first connection terminal 15 of the electronic control unit 5 via the wiring line 61.

An insulating layer (not shown) mainly formed of an insulating material (e.g., alumina) is interposed between the oxygen pump cell 14 and the oxygen-concentration detection cell 24 so as to electrically insulate the cells 14 and 24 from each other. A porous diffusion layer 18 is provided at a portion of the insulating layer. The porous diffusion layer 18 is mainly formed of an insulating material (e.g., alumina) such that the porous diffusion layer 18 becomes porous so as to limit the rate of diffusion of the object gas introduced into the interior of the sensor element 10. Notably, instead of providing the porous diffusion layer 18, a small hole may be provided in the side wall of the insulating layer as a diffusion rate limiting section.

A hollow measurement chamber 20 is formed between the oxygen pump cell 14 and the oxygen-concentration detection cell 24, and surrounded by the porous diffusion layer 18 and the above-described insulating layer (not shown). The measurement chamber 20 communicates with a measurement gas atmosphere via the porous diffusion layer 18 (specifically, its porous portion). The second pump electrode 16 is located on the upper wall of the measurement chamber 20 and exposed to the interior of the measurement chamber 20, and the first detection electrode 22 is located on the lower wall of the measurement chamber 20 and exposed to the interior of the measurement chamber 20.

Further, a reinforcing plate 30 is stacked on a surface of the oxygen-concentration detection cell 24 opposite its surface facing the measurement chamber 20, to thereby increase the overall strength of the sensor element 10. The reinforcing plate 30 is substantially the same in size as the solid electrolyte bodies 13 and 23, and is formed into a plate-like shape from a material mainly made of ceramic.

The second detection electrode 28 is sandwiched between the reinforcing plate 30 and the oxygen-ion-conductive solid electrolyte body 23. Thus, the second detection electrode 28 is isolated from the outside, and a reference oxygen chamber (closed space) 26 is formed around the second detection electrode 28. Accordingly, through supply of a constant minute current Icp which flows from the second detection electrode 28 toward the first detection electrode 22, oxygen is pumped from the measurement chamber 20 toward the second detection electrode 28 side, whereby oxygen of a substantially constant concentration is accumulated within the reference oxygen chamber 26. In this manner, the oxygen within the reference oxygen chamber 26 provides a reference concentration for detection of oxygen concentration.

Meanwhile, the heater 43, which assume the form of a flat plate, is disposed to face the oxygen pump cell 14 of the sensor element 10. The heater 43 is formed from a material mainly made of alumina, and includes a heater wiring 72 formed from a material mainly made of platinum. By means of voltage (electrical power) supplied from a heater control circuit 60 to be described later, the heater 43 is controlled such that the temperature of the sensor element 10 becomes equal to or higher than an activation temperature (in this embodiment, 830° C.). Opposite ends of the heater wiring 72 are electrically connected to the heater control circuit 60.

Through heating by the heater 43, the sensor element 10 (the oxygen pump cell 14 and the oxygen-concentration detection cell 24 thereof) is activated, whereby gas detection (oxygen detection) becomes possible.

Next, operation of the gas sensor 8 (the sensor element 10) will be described.

The object gas (exhaust gas) diffuses into the measurement chamber 20 via the porous diffusion layer 18. At that time, in a state where the air-fuel mixture supplied to the engine (that is, the object gas within the measurement chamber 20) is maintained at the theoretical air-fuel ratio, an electromotive force of 450 mV is generated in the oxygen-concentration detection cell 24 (a potential difference of 450 mV is generated between the first detection electrode 22 and the second detection electrode 28) because of a difference in oxygen concentration between the measurement chamber 20 and the reference oxygen chamber 26, which provides a reference oxygen concentration.

Incidentally, the concentration of oxygen contained in the exhaust gas changes in accordance with the air-fuel ratio of the air-fuel mixture supplied to the engine, and the oxygen concentration of the object gas contained in the measurement chamber 20 also changes. In view of this phenomenon, in the internal-combustion-engine control system 1 of the present embodiment, the sensor control circuit 2 controls Ip current flowing through the oxygen pump cell 14 such that the potential difference between the first detection electrode 22 and the second detection electrode 28 is maintained at 450 mV. That is, as a result of controlling the Ip current such that the air-fuel ratio of the object gas within the measurement chamber 20 becomes equal to the theoretical air-fuel ratio, the oxygen pump cell 14 pumps oxygen.

The oxygen pump cell 14 is configured to pump oxygen out of the measurement chamber 20 or pump oxygen into the measurement chamber 20 depending on the flow direction of the current flowing between the pair of electrodes (the first pump electrode 12 and the second pump electrode 16). Also, the oxygen pump cell 14 is configured to adjust the rate of pumping of oxygen in accordance with the magnitude of the current flowing between the pair of electrodes. Therefore, the concentration of oxygen contained in the object gas can be computed on the basis of the flow state (the flow direction, magnitude, etc.) of the Ip current.

Figure 2:
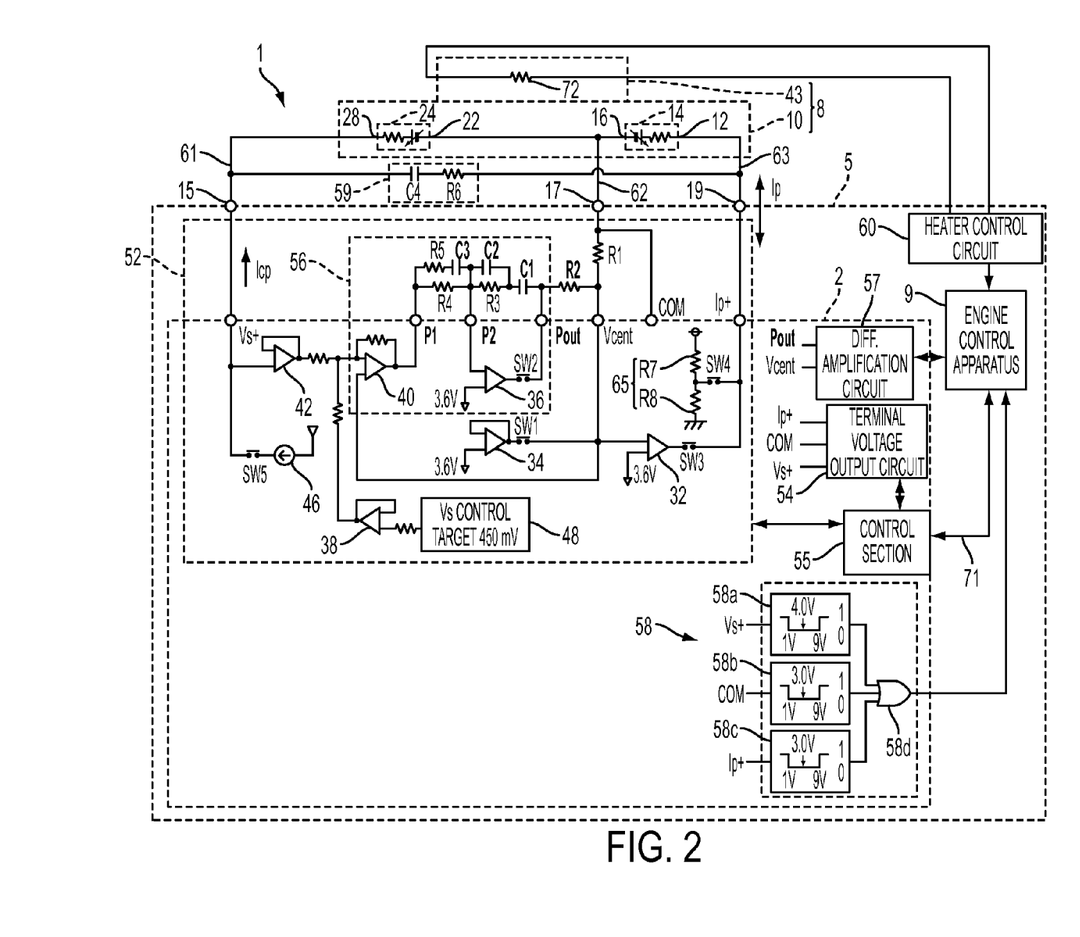
FIG. 2 Circuit diagram schematically showing the configuration of the electronic control unit.

Next, the configuration and operation of the electronic control unit 5 will be described with reference to FIG. 2. FIG. 2 is a circuit diagram schematically showing the configuration of the electronic control unit 5. As described above, the electronic control unit 5 includes the sensor control circuit 2, the heater control circuit 60, and the engine control apparatus 9.

The sensor control circuit 2 includes a sensor drive circuit 52, a terminal voltage output circuit 54, the control section 55, a differential amplification circuit 57, and an anomaly detection circuit 58.

The sensor drive circuit 52 includes an operational amplifier 32 for supplying the Ip current for driving the oxygen pump cell 14, a PID control circuit 56 for improving the control characteristics of the Ip current, a constant current source 46 for supplying a constant current Icp to the oxygen-concentration detection cell 24 so as to maintain a constant oxygen concentration around the second detection electrode 28 (in the reference oxygen chamber 26), and a constant voltage source 48 for supplying a control target voltage associated with the Ip current.

Further, the sensor drive circuit 52 includes connection terminals (the Vs+ terminal, the COM terminal, and the Ip+ terminal) for connection with the sensor element 10, terminals (a P1 terminal, a P2 terminal, and a Pout terminal) to which elements for determining the characteristics of the PID control circuit 56 are externally connected, and switch SW1 to SW5 for changing the energization state (operation mode) of the sensor drive circuit 52 in accordance with an energized-state switching instruction output from the engine control apparatus 9. Notably, the operation mode of the sensor drive circuit 52 represents the state of supply of electricity to the sensor element 10.

Moreover, the sensor drive circuit 52 includes a Vcent point connected to the COM terminal 17. An output end of the PID control circuit 56 to be described later, the inverting input terminal of an operational amplifier 32, and the output terminal of an operational amplifier 34 are connected to the Vcent point. Notably, the output terminal of the operational amplifier 34 is connected to the Vcent terminal via the switch SW1. Further, the inverting input terminal of the operational amplifier 34 is connected to the output terminal thereof, and a reference voltage of 3.6 V is applied to the non-inverting input terminal of the operational amplifier 34. That is, the operational amplifier 34 applies the reference voltage of 3.6 V to the Vcent terminal, and supplies an anomaly analysis current for anomaly analysis for the sensor element 10 and the like current.

Notably, the second pump electrode 16 is connected to the Vcent point via the wiring line 62, the second connection terminal 17, and a resistor R1.

A voltage division circuit 65 and the output terminal of the operational amplifier 32 are connected to the Ip+ terminal. The voltage division circuit 65 includes two resistors R7 and R8 for dividing a constant power supply voltage, and the connection point between the resistors R7 and R8 is connected to the Ip+ terminal via the switch SW4. Further, the output terminal of the operational amplifier 32 is connected to the Ip+ terminal via the switch SW3. Notably, one end of the resistor R8 is grounded.

The PID control circuit 56 is connected to the inverting input terminal of the operational amplifier 32 via the Vcent terminal and a resistor R2, and the reference voltage of 3.6 V is applied to the non-inverting input terminal of the operational amplifier 32. That is, the operational amplifier 32 constitutes a portion of a negative feedback circuit which controls the supply of current to the sensor element 10.

The PID control circuit 56 has a function of performing PID computation for the deviation $\Delta Vs$ between 450 mV, which is the control target voltage of the oxygen-concentration detection cell 24 and the output voltage Vs of the oxygen-concentration detection cell 24 to thereby improve the control characteristics of the above-described negative feedback control. The PID control circuit 56 includes operational amplifiers 36 and 40, resistor R3 to R5, and capacitor C1 to C3.

The output terminal of the operational amplifier 42 is connected to the input terminal of the PID control circuit 56 (the inverting input terminal of the operational amplifier 40), and the non-inverting input terminal of the operational amplifier 42 is connected to the Vs+ terminal. That is, the output voltage Vs of the oxygen-concentration detection cell 24 is input to the PID control circuit 56 via the operational amplifier 42. Notably, the inverting input terminal of the operational amplifier 42 is connected to the output terminal thereof.

Moreover, the constant current source 46 is connected to the Vs+ terminal via the switch SW5. The constant current source 46 supplies a constant current Icp (e.g., 17 μA) to the oxygen-concentration detection cell 24 so as to maintain constant the oxygen concentration around the second detection electrode 28 of the oxygen-concentration detection cell 24 (within the reference oxygen chamber 26).

Further, the output terminal of the operational amplifier 38 is connected to the inverting input terminal of the operational amplifier 40 via a resistor. The constant voltage source 48 is connected to the non-inverting input terminal of the operational amplifier 38, and the inverting input terminal of the operational amplifier 38 is connected to the output terminal thereof. That is, the output of the constant voltage source 48 is input to the inverting input terminal of the operational amplifier 40 via the operational amplifier 38, whereby a voltage of 450 mV, which serves as a control target used for controlling the Ip current, is supplied to the PID control circuit 56 via the operational amplifier 40.

The output terminal of the operational amplifier 40 is connected to the P1 terminal, and the non-inverting input terminal of the operational amplifier 40 is connected to the Vcent terminal. Further, a resistor is interposed between the output terminal of the operational amplifier 40 and the inverting input terminal thereof. A first series circuit including a resistor R5, a capacitor C3, and a capacitor C2 and a second series circuit including resistors R4 and R3 are connected in parallel with each other, and the resistor R5 side end of the first series circuit and the resistor R4 side end of the second series circuit are connected in parallel to the P1 terminal. Further, the connection point between the capacitors C3 and C2 of the first series circuit is connected to the P2 terminal. Similarly, the connection point between the resistors R4 and R3 of the second series circuit is connected to the P2 terminal. Moreover, the capacitor C2 and the resistor R3 are connected to the capacitor C1, which is connected to the Pout terminal.

The P2 terminal is connected to the inverting input terminal of the operational amplifier 36, the output end of the PID control circuit 56 (the output terminal of the operational amplifier 36) is connected to the Pout terminal via the switch SW2. The reference voltage of 3.6 V is applied to the non-inverting input terminal of the operational amplifier 36.

The Pout terminal is connected to the Vcent point via the resistor R2, and the output end of the PID control circuit 56 (the capacitor C1) is connected to the COM terminal via the resistor R2 and the resistor R1.

Notably, the resistors R3 to R5 and the capacitors C1 to C3 are attached to the P1 terminal and the P2 terminal so as to determine the control characteristics of the PID control circuit 56.

Further, an oscillation prevention circuit 59 composed of a series circuit including a resistor R6 and a capacitor C4 is interposed between the Vs+ terminal and the Ip+ terminal in order to prevent oscillation of the sensor drive circuit 52.

Next, other circuits 54, 57, and 58 contained in the sensor control circuit 2 will be described.

The terminal voltage output circuit 54 outputs respective terminal voltages of the Vs+ terminal, the COM terminal, and the Ip+ terminal to the engine control apparatus 9 via the control section 55. Notably, although connection lines are omitted in FIG. 2, the input terminals of the terminal voltage output circuit 54 are connected to the Vs+ terminal, the COM terminal, and the Ip+ terminal, respectively.

The differential amplification circuit 57 outputs the voltage generated across the resistor R2 (specifically, the voltage generated between the Vcent point and the Pout point) to the input port of the engine control apparatus 9 as a gas detection signal. This voltage is a voltage obtained through current-to-voltage conversion of the Ip current flowing through the oxygen pump cell 14, which conversion is effected by the resistor R2. Notably, the gas detection signal may be output to the input port of the engine control apparatus 9 via the transmission cable 71.

The anomaly detection circuit 58 is composed of window comparators 58*a*, 58*b*, and 58*c* and an OR circuit 58*d*. The output terminals of the comparators 58*a*, 58*b*, and 58*c* are connected to the input terminals of the OR circuit 58*d*. Although connection lines are omitted in FIG. 2, the input terminals of the comparators are connected to the Vs+ terminal, the COM terminal, and the Ip+ terminal, respectively.

The window comparator 58*a* (58*b*, 58*c*) is configured to output a low-level signal when the terminal voltage of the Vs+ terminal (the COM terminal, the Ip+ terminal) is within a predetermined voltage range, and output a high-level signal when the terminal voltage of the Vs+ terminal (the COM terminal, the Ip+ terminal) is outside the predetermined voltage range.

The terminal voltage of the Vs+ terminal is usually maintained at 4.05 V, which is the sum of the reference voltage (3.6 V) of the COM terminal and the output voltage Vs (450 mV) of the oxygen-concentration detection cell 24. However, when the wiring line 61 or the like connected to the Vs+ terminal (also referred to as the Vs+ line) is short-circuited to the power supply potential or the ground potential due to some cause, the terminal voltage of the Vs+ terminal becomes equal to the power supply potential or the ground potential. As a result, an excessively large anomalous current flows through the sensor element 10, and the sensor element 10 may be broken. In view of this, the window comparator 58*a* is configured to compare the terminal voltage of the Vs+ terminal with preset thresholds, and output a high-level signal when the terminal voltage of the Vs+ terminal changes beyond the thresholds.

Specifically, the upper threshold of the window comparator 58*a* is set to 9 V or a predetermined voltage obtained by subtracting a predetermined value (e.g., 1.5 V) from the power supply voltage in consideration of fluctuation in the power supply voltage of the sensor element control circuit 50, and the lower threshold is set to 1 V in consideration of the ground level of 0 V and drifting of the ground level therefrom. When the terminal voltage of the Vs+ terminal increases above the upper limit (9 V or the predetermined voltage) or decreases below the lower limit (1 V), the window comparator 58*a* output a high-level signal.

The terminal voltage of the COM terminal is usually controlled by the operational amplifier 32 such that it becomes equal to the reference voltage of 3.6 V. However, when the wiring line 62 or the like connected to the COM terminal (also referred to as a COM line) is short-circuited to the power supply voltage or the ground level due to some cause, as in the case of the Vs+ terminal, the terminal voltage of the COM terminal becomes equal to the power supply potential or the ground potential. In view of this, the window comparator 58*b* is configured to compare the terminal voltage of the COM terminal with preset thresholds, and output a high-level signal when the terminal voltage of the COM terminal changes beyond the thresholds. Specifically, as in the case of the wind comparator 58*a*, the upper threshold of the window comparator 58*b* is set to 9 V or the predetermined voltage, and the lower threshold thereof is set to 1 V. When the terminal voltage of the COM terminal increases above the upper limit (9 V or the predetermined voltage) or decreases below the lower limit (1 V), the window comparator 58*b* output a high-level signal.

Even in the case of Ip+ terminal, when the wiring line 63 or the like connected to the Ip+ terminal (also referred to as an Ip+ line) is short-circuited to the power supply voltage or the ground level due to some cause, the terminal voltage of the Ip+ terminal becomes equal to the power supply potential or the ground potential. In view of this, the window comparator

58c is configured to compare the terminal voltage of the Ip+ terminal with preset thresholds, and output a high-level signal when the terminal voltage of the Ip+ terminal changes beyond the thresholds. Specifically, as in the case of the wind comparator 58b, for the wind comparator 58c to which the terminal voltage of the Ip+ terminal is input, the upper threshold is set to 9 V or the predetermined voltage and the lower threshold is set to 1 V such that the reference voltage of 3.6 V is between the lower and upper and thresholds. When the terminal voltage of the Ip+ terminal increases above the upper limit (9 V or the predetermined voltage) or decreases below the lower limit (1 V), the window comparator 58c output a high-level signal.

The OR circuit 58d logically adds the signals from the window comparators 58a, 58b, and 58c. That is, when the OR circuit 58d receives a high-level signal from any one of the window comparators 58a, 58b, and 58c, the OR circuit 58d sets an anomaly detection flag DIAG to 1, and outputs it to the engine control apparatus 9. Notably, when each of the terminal voltages of the Vs+ terminal, the COM terminal, and the Ip+ terminal falls within the predetermined voltage range, the anomaly detection circuit 58 sets the anomaly detection flag DIAG to 0, and outputs it to the engine control apparatus 9. As described above, the anomaly detection circuit 58 has a function of setting the anomaly detection flag DIAG to 1 when a short-circuit anomaly occurs in any of the Vs+ line, the COM line, and the Ip+ line, with the result that the terminal voltage of the Vs+ terminal, the COM terminal, or the Ip+ terminal changes beyond the thresholds and assumes an anomalous voltage value (in other words, an anomaly occurs in the sensor element 10).

The sensor drive circuit 52 having the above-described configuration switches the ON/OFF states of the switches SW1 to SW5 in accordance with instructions from the engine control apparatus 9, to thereby set the energization state (operation mode) of the sensor drive circuit 52 itself to one of an energization state for gas concentration measurement, an energization state for sensor protection, and a pre-activation energization state. These energization states will be described later.

Notably, the engine control apparatus 9 outputs instructions for switching the energization state of the sensor drive circuit 52 (specifically, control signals for turning the switches SW1 to SW5 ON and OFF) from the output port. The instructions are fed to the sensor control circuit (the control section 55 thereof) via the transmission cable 71. The control section 55 switches (sets) the energization state of the sensor drive circuit 52.

Accordingly, the control section 55 and the switches SW1 to SW5 correspond to the "setting unit" in the claims. Further, the instruction for setting the sensor drive circuit 52 to the energization state for sensor protection (deenergization state) corresponds to the "deenergization instruction" in the claims, and the instruction for setting the sensor drive circuit 52 to the pre-activation energization state (energization state) corresponds to the energization instruction in the claims.

Further, the gas detection signal representing the voltage generated across the resistor R2 is input to the input port of the engine control apparatus 9 via the differential amplification circuit 57. Moreover, the anomaly detection flag DIAG from the anomaly detection circuit 58 is directly input to the input port of the engine control apparatus 9. Meanwhile, the output signal from the terminal voltage output circuit 54 is input to the control section 55, and then input to the input port of the engine control apparatus 9 via the transmission cable 71. Notably, although not shown in FIG. 2, an element resistance signal, which represents the internal resistance of the sensor element 10, separately detected by a known method is also input to the control section 55, and then input to the input port of the engine control apparatus 9 via the transmission cable 71.

As described above, the engine control apparatus 9 can control the energization state of the sensor drive circuit 52, and can detect the presence/absence of anomaly of the sensor element 10 on the basis of the input signals from the anomaly detection circuit 58 and the terminal voltage output circuit 54. Specifically, the engine control apparatus 9 can detect a terminal having an anomaly and the details of the anomaly (power supply short circuit (VB short circuit), ground short circuit) by comparing the state of each input terminal voltage with predetermined determination conditions to find a condition that matches the state.

Figure 3:
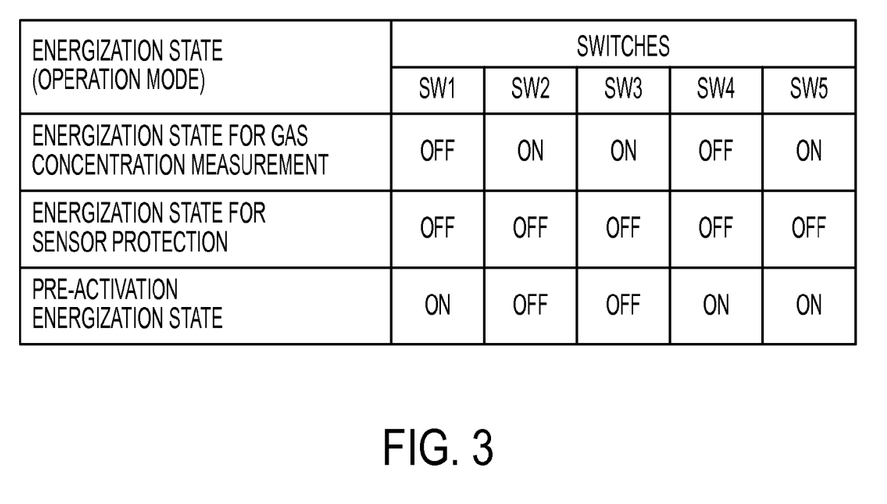
FIG. 3 Explanatory table showing the states of switches for various energization states (operation modes).

Next, the energization states (operation modes) to which the sensor drive circuit 52 can be set through switching of the ON/OFF states of the switches SW1 to SW5 will be described with reference to FIG. 3.

Here, the energization state for sensor protection is a state in which the sensor drive circuit 52 cuts off the electrical connection between the sensor element 10 and the sensor drive circuit 52 so as to prevent current from flowing into the gas sensor 8, to thereby protect the gas sensor 8.

The energization state for gas concentration measurement is a state in which the sensor drive circuit 52 controls the magnitude and direction of current flowing through the oxygen pump cell 14 such that the voltage between the two electrodes of the oxygen-concentration detection cell 24 assumes a desired value, to thereby enable the gas concentration measurement to be performed.

The pre-activation energization state is a state in which the sensor drive circuit 52 supplies a minute current to the two electrodes of at least one of the oxygen-concentration detection cell 24 and the oxygen pump cell 14 such that an overvoltage is not applied to the gas sensor 8 (the two cells 14 and 24 thereof). In the case of a gas sensor configured such that one electrode 28 of the oxygen-concentration detection cell 24 opposite the measurement chamber is isolated from the outside, a more specific example of the pre-activation energization state is an energization state in which the sensor drive circuit 52 supplies a minute current to the oxygen-concentration detection cell 24 so as to cause the electrode 28 to function as an internal reference oxygen source.

Notably, the energization state for sensor protection corresponds to the "deenergization state" in the claims, and the energization state for gas concentration measurement and the pre-activation energization state correspond to the energization state" in the claims.

First, in the energization state for gas concentration measurement, the switches SW2, SW3, and SW5 of the sensor drive circuit 52 are turned ON, and the switches SW1 and SW4 of the sensor drive circuit 52 are turned OFF. The energization state for gas concentration measurement corresponds to an operation mode for setting the sensor drive circuit 52 to a state in which it can supply a relatively large current to the gas sensor 8 (specifically, the oxygen pump cell 14) for the purpose of, for example, pumping of oxygen. The maximum current which can be supplied to the oxygen pump cell 14 is determined from the current drive capacities of the operational amplifier 32 and the operational amplifier 36. In the present embodiment, the maximum current is set to about 20 mA.

When the object gas enters a state in which supply of fuel is excessive (rich state), the oxygen concentration within the measurement chamber 20 becomes lower than a level corresponding to the theoretical air-fuel ratio, and the output voltage Vs of the oxygen-concentration detection cell 24 becomes higher than 450 mV, which is the control target voltage. Accordingly, a deviation ΔVs between the control target voltage and the output voltage Vs is generated, and the deviation ΔVs undergoes the PID computation performed by the PID control circuit 56. The deviation ΔVs having undergone the PID computation is fed back by the operational amplifier 32. As a result, an Ip current for causing the oxygen pump cell 14 to pump oxygen into the measurement chamber 20 for making up the shortage of oxygen flows through the oxygen pump cell 14.

Meanwhile, the object gas enters a state in which supply of fuel is insufficient (lean state), the oxygen concentration within the measurement chamber 20 becomes higher than the level corresponding to the theoretical air-fuel ratio, and the output voltage Vs of the oxygen-concentration detection cell 24 becomes lower than 450 mV, which is the control target voltage. Accordingly, as in the above-described case, the deviation ΔVs is fed back by the operational amplifier 32, and an Ip current for causing the oxygen pump cell 14 to pump an excessive portion of oxygen from the measurement chamber 20 flows through the oxygen pump cell 14.

In this manner, the oxygen concentration within the object gas can be computed on the basis of the state of flow of the Ip current (the flow direction and magnitude of the Ip current).

Next, in the energization state for sensor protection, all the switches SW1 to SW5 of the sensor drive circuit 52 are turned OFF. Therefore, the supply of the signals from the operational amplifiers 32, 34, 36 and the constant current source 46 to the sensor element 10 is stopped, whereby the supply of electricity from the sensor drive circuit 52 to the sensor element 10 is stopped. Accordingly, when a wiring anomaly occurs, by means of the setting the sensor drive circuit 52 to the energization state for sensor protection in accordance with an instruction from the engine control apparatus 9, it is possible to prevent anomalous current from continuously flowing through the sensor element 10, to thereby protect the sensor element 10.

In the pre-activation energization state, the switches SW1, SW4, and SW5 of the sensor drive circuit 52 are turned ON, and the switches SW2 and SW3 of the sensor drive circuit 52 are turned OFF. Since the switch SW3 is OFF, no current is supplied from the operational amplifier 32, which drives the oxygen pump cell 14. Further, since the switch SW2 is OFF, no current is supplied from the operational amplifier 36. As a result, the current control (feedback control) for the oxygen pump cell 14 on the basis of the output of the oxygen-concentration detection cell 24 is stopped.

Further, since the switches SW1, SW4, and SW5 are ON, minute constant currents Icp are supplied from the operational amplifier 34, the constant current source 46, and the voltage division circuit 65 to the oxygen pump cell 14 and the oxygen-concentration detection cell 24. As a result, oxygen is pumped from the first detection electrode 22 toward the second detection electrode 28, whereby oxygen having a substantially constant concentration is accumulated in the reference oxygen chamber 26 formed around the second detection electrode 28.

As described above, in the pre-activation energization state, only a minute current is supplied to the sensor element 10. Therefore, even when a wiring anomaly occurs, an excessively large current is not supplied to the sensor element 10, and breakage (blackening, etc.) of the sensor element 10 becomes less likely to occur.

Further, as described above, the engine control apparatus 9 detects a wiring anomaly on the basis of the state of each of the input terminal voltages. In the pre-activation energization mode, since each terminal voltage is low, such a wiring anomaly can be detected without causing breakage of the sensor element 10.

For example, the sensor drive circuit 52 is set to the energization state for gas concentration measurement in a state where, for example, the wiring line 62 is short-circuited to the ground; i.e., the wiring line 62 has a wiring anomaly, there is formed an electrical path extending from the operational amplifier 32 to the ground line via the oxygen pump cell 14 and the wiring line 62, and the maximum current, which corresponds to the current drive capacity of the operational amplifier 32, is supplied from the operational amplifier 32 to the oxygen pump cell 14. In this case, an excessively large current is supplied to the oxygen pump cell 14, whereby breakage (blackening or the like) of the sensor element 10 occurs within a short period of time. In contrast, if the sensor drive circuit 52 is in the pre-activation energization state when the wiring line 62 is short-circuited to the ground, the current supplied from the voltage division circuit 65 to the oxygen pump cell 14 is very small, although an electrical path extending from the voltage division circuit 65 to the ground line via the oxygen pump cell 14 and the wiring line 62 is formed. Therefore, it is possible to prevent supply of an excessively large current to the oxygen pump cell 14, and prevent breakage (blackening or the like) of the sensor element 10 from occurring within a short period of time.

Next, there will be described the details of anomaly final determination processing, which is the feature of the present invention and which is performed by the engine control apparatus 9 (more specifically, the CPU of the engine control apparatus 9).

In the present invention, even when a wiring anomaly of the gas sensor is detected one time, the engine control apparatus 9 does not finally determine that an anomaly has occurred, and does not take necessary measures, such as stopping the operation of the sensor. Instead, the engine control apparatus 9 causes the sensor drive circuit 52 to return to the energization state, and again detects the presence/absence of a wiring anomaly, to thereby prevent erroneous detection of a wiring anomaly.

Notably, in the present embodiment, sensor energization control processing is executed in the engine control apparatus 9 as a main routine, and the above-mentioned anomaly final determination processing is called as a sub-routine and executed. Accordingly, the sensor energization control processing, which is the main routine, will be first described.

First, the engine control apparatus 9 starts when the power supply of the internal-combustion-engine control system 1 is turned ON, and executes initialization processing (initialization of internal variables, etc.). After completion of the initialization processing, the engine control apparatus 9 starts various types of control processings as follows.

The various types of control processings include specific-gas-concentration detection processing for detecting the concentration of a specific gas (oxygen) contained in the exhaust gas on the basis of the gas detection signal from the sensor control circuit 2, etc.; instruction output processing for outputting to the sensor control circuit 2 instructions for switching the energization state; and air-fuel-ratio control processing for performing air-fuel-ratio control for the engine through use of the concentration of the specific gas detected on the basis of the gas detection signal.

When the power supply of the automobile is turned ON, the engine control apparatus 9 starts processing. After completion of the initialization processing, as one of the various control processings, the engine control apparatus 9 executes the sensor energization control processing for controlling the state of supply of electricity to the sensor element 10. In the sensor energization control processing, the engine control apparatus 9 determines or selects an optimal energization state, as the state of supply of electricity to the sensor element 10, on the basis of various conditions, and executes processing for outputting to the sensor control circuit 2 a switching instruction corresponding to the selected energization state.

The optimal energization state is selected as follows. For example, immediately after the start up of the sensor, the engine control apparatus 9 selects the pre-activation energization state as the optimal energization state. Under the conditions where the sensor element 10 enters an activated state, the engine control apparatus 9 selects the energization state for gas concentration measurement as the optimal energization state.

Meanwhile, when a wiring anomaly (short circuiting of a wiring line, etc.) occurs, the engine control apparatus 9 executes the anomaly final determination processing to be described later.

The engine control apparatus 9 receives from the sensor control circuit 2 a present state flag representing the present energization state, and can know the present energization state from the present state flag. Notably, the embodiment may be modified such that the engine control apparatus 9 recognizes the present energization state of the sensor control circuit 2 by itself, and recognizes the state of supply of electricity to the sensor element 10 without receiving the present state flag from the sensor control circuit 2.

A more specific method of determining or selecting the optimal energization state will be described. The engine control apparatus 9 determines whether or not the gas sensor has been activated on the basis of the element resistance signal of the gas sensor. When the gas sensor has not yet been activated, the engine control apparatus 9 selects the pre-activation energization state as the optimal energization state. When the gas sensor has already been activated, the engine control apparatus 9 selects the energization state for gas concentration measurement as the optimal energization state. When the anomaly detection circuit 58 determines that an anomaly has occurred in the gas sensor or the electricity supply path, the engine control apparatus 9 performs the anomaly final determination processing, which will be described later. Further, when the anomaly detection circuit 58 determines that the anomaly of the gas sensor or the electricity supply path has disappeared, the engine control apparatus 9 determines the optimal energization state on the basis of the element resistance signal of the gas sensor.

Notably, the element resistance signal refers to a signal obtained as follows. Current or voltage having a predetermined magnitude is periodically supplied to either one of the oxygen pump cell 14 and the oxygen-concentration detection cell 24 of the gas sensor 8, and a signal obtained through the cell at that time is used as the element resistance signal. Since this element resistance signal can be obtained by making use of a known method (circuit configuration), the method of obtaining the element resistance signal will not be described in detail in the embodiment. However, the method will be described briefly. Current of a predetermined magnitude is periodically supplied to the oxygen-concentration detection cell 24, and an output obtained through the oxygen-concentration detection cell 24 at that time is sampled and held. The sampled and held output is supplied to the engine control apparatus 9 as the element resistance signal.

Figure 4:
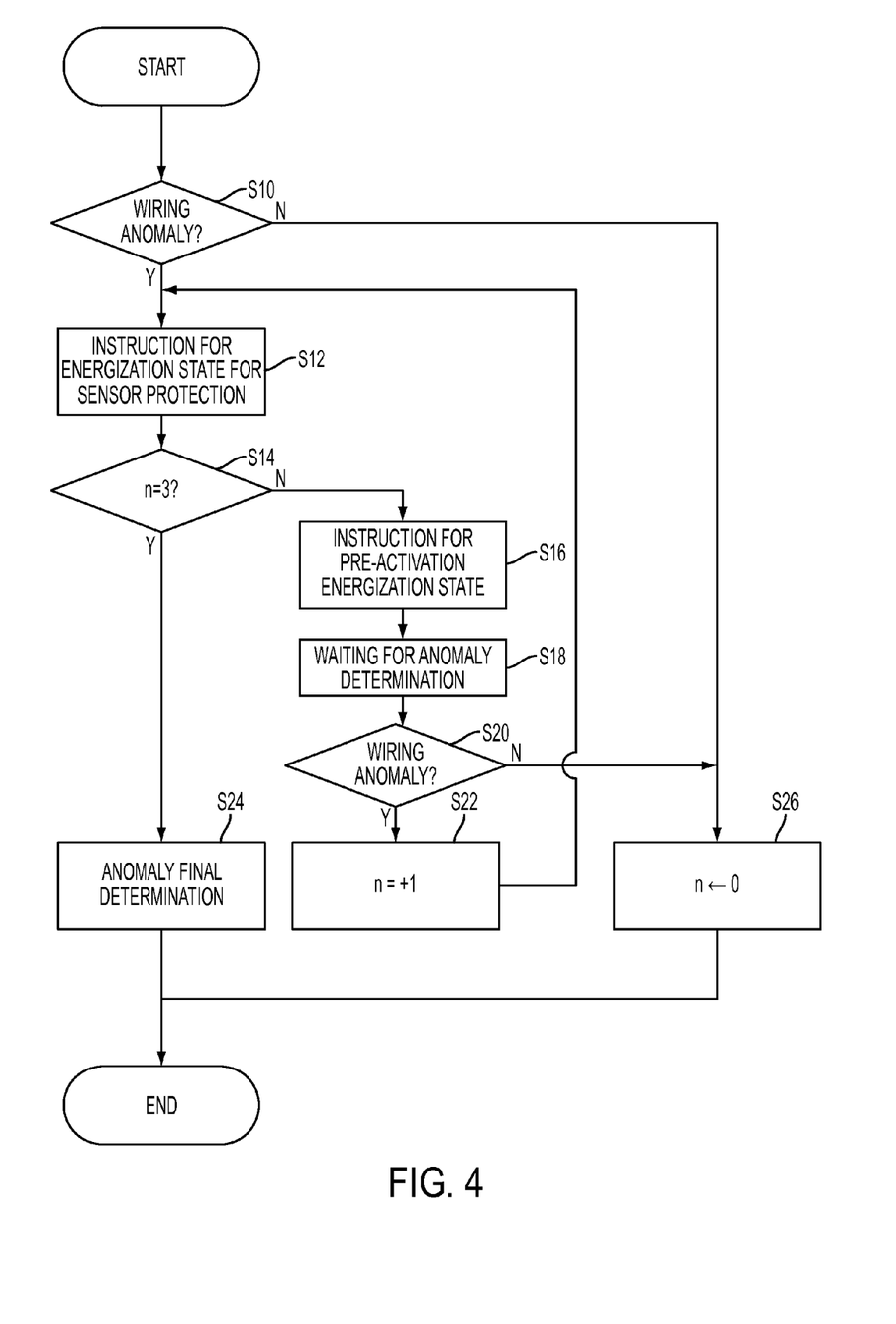
FIG. 4 Flowchart showing anomaly final determination processing according to a first embodiment.

Next, the above-mentioned anomaly final determination processing will be described with reference to FIG. 4.

When the anomaly final determination processing is started, the engine control apparatus 9 first determines, on the basis of the results of determination in the sensor energization control processing (the main routine), whether or not a wiring anomaly of the gas sensor 8 or the sensor drive circuit 52 is detected by the anomaly detection circuit (step S10).

When a wiring anomaly is detected in step S10, the engine control apparatus 9 proceeds to step S12, and outputs, from the output port to the control section 55, an instruction for switching the sensor drive circuit 52 to the energization state for sensor protection (the deenergization state). The step S12 is a processing step for protecting the gas sensor when a wiring anomaly is detected. After completion of initialization processing similar to that performed by the engine control apparatus 9, the control section 55 receives the above-mentioned instruction, and sets the ON/OFF states of the witches SW1 to SW5 of the sensor drive circuit 52.

Meanwhile, a wiring anomaly is not detected in step S10, the engine control apparatus 9 proceeds to step S26.

After having proceeded from step S12 to step S14, the engine control apparatus 9 determines whether or not an anomaly count n is equal to 3. The anomaly count n is incremented in step S22 to be described later, and is cleared in step S26.

When it is determined in step S14 that n=3, the engine control apparatus 9 proceeds to step S24, and finally determines that an anomaly has occurred, and ends the processing. When the engine control apparatus 9 finally determines that an anomaly has occurred, it performs processing, for example, for turning a sensor anomaly lamp on while maintaining the energization state for sensor protection.

Meanwhile, when it is determined in step S14 that n is not equal to 3, the engine control apparatus 9 proceeds to step S16, and outputs, from the output port to the control section 55, an instruction for switching the sensor drive circuit 52 to the pre-activation energization state (the energization state). Notably, in the present invention, no limitation is imposed on the "energization state" in step S16 (i.e., the energization state for gas concentration measurement or the pre-activation energization state may be selected as the energization state) so long as electricity is supplied to the gas sensor. However, selecting the pre-activation energization state is preferred, because direct switching from the energization state for sensor protection set in step S12 to the energization state for gas concentration measurement may result in breakage of the sensor.

Next, the engine control apparatus 9 proceeds to step S18, and performs anomaly determination waiting processing for a predetermined period of time. This anomaly determination waiting processing is provided for waiting and seeing whether or not the anomaly state of the gas sensor changes after the supply of electricity to the gas sensor 8 in step S16, instead of finally determining, immediately after detection of a wiring anomaly in step S10, that an anomaly has occurred. By virtue of this operation, it is possible to prevent erroneous detection of a wiring anomaly and prevent meaningless stoppage of the sensor in the case where the wiring anomaly disappears immediately, and the normal state is restored. The waiting time in step S18 may be counted by making use of a timer provided in the engine control apparatus 9.

Next, the engine control apparatus 9 proceeds to step S20, and determines whether or not a wiring anomaly of the gas sensor 8 or the sensor drive circuit 52 is detected again by the anomaly detection circuit 58. The processing of the step S20 is processing for determining whether or not the state of the gas sensor has changed and the wiring anomaly has disappeared during the period of waiting in step S18. When a wiring anomaly is not detected in step S20, the engine control apparatus 9 proceeds to step S26. In step S26, the engine control apparatus 9 determines that no wiring anomaly has occurred, ends the processing, and resets the anomaly count n to 0. After completion of the processing of step S26, the engine control apparatus 9 returns to the sensor energization control processing, which is the main routine.

Meanwhile, when a wiring anomaly is detected in step S20, the engine control apparatus 9 proceeds to step S22 so as to increment the anomaly count n, and returns to step S12.

The above-described processing in steps S12 to S16 executed by the engine control apparatus 9 corresponds to the "return-from-anomaly checking processing" in the claims, and the processing of step S20 corresponds to the "determination processing" in the claims. The return-from-anomaly checking processing is processing adapted to effect switching from the energization state for sensor protection (the deenergization state) to the pre-activation energization state (the energization state) when a wiring anomaly is detected and perform the anomaly determination waiting processing for a predetermined period of time so as to check whether or not the sensor has returned from the anomalous state (the wiring anomaly has disappeared).

As described above, even when a wiring anomaly of the gas sensor is detected once, the engine control apparatus 9 does not immediately determines that an anomaly has occurred, and does not perform necessary measures such as stopping the operation of the sensor. Instead, the engine control apparatus 9 returns the state of the sensor drive circuit to the energization state, and then again determines whether or not a wiring anomaly is present. Thus, it becomes possible to prevent erroneous detection of a wiring anomaly and prevent meaningless stoppage of the sensor in the case where the wiring anomaly disappears immediately.

Notably, in this embodiment, when the engine control apparatus 9 determines in step S14 that n=3, it finally determines that an anomaly has occurred. Therefore, the engine control apparatus 9 repeats the return-from-anomaly checking processing three times at the most, to hereby increase the possibility of disappearance of a wiring anomaly or the like. The present embodiment may be modified to perform the return-from-anomaly checking processing only one time (in step S14, n=1 is used as a determination criteria). However, when the return-from-anomaly checking processing is performed two times or more, erroneous detection of a wiring anomaly and a temporary wiring anomaly become more likely to disappear. Therefore, there can be suppressed the occurrence of a state where the operation of the sensor is stopped every time a wiring anomaly is detected and the sensor requires wasteful time to resume the gas-concentration-measurement operation.

Further, in this embodiment, when the count n is incremented to 3 in step S22, the engine control apparatus 9 returns to step S12 so as to effect switching from the pre-activation energization state (the energization state) to the energization state for sensor protection (the deenergization state). After the switching to the deenergization state is completed, the engine control apparatus 9 finally determines in step S24 that an anomaly has occurred. By virtue of this operation, the occurrence of an anomaly is finally determined after the supply of electricity to the gas sensor is stopped so as to protect the sensor. Therefore, breakage of the gas sensor can be prevented more reliably.

Notably, in the present embodiment, the anomaly detection circuit 58, the engine control apparatus 9, and the processing of step S10 executed by the engine control apparatus 9 correspond to the "wiring anomaly detection unit" described in the claims. Further, the processing of step S10 for determining whether or not a wiring anomaly is detected by the anomaly detection circuit 58 corresponds to the "wiring anomaly detection step" described in the claims.

Further, in the present embodiment, the engine control apparatus 9 and the series of processings of step S12 to S22 executed by the engine control apparatus 9 correspond to the "determination unit" described in the claims, and the series of processings of step S12 to S22 correspond to the "determination step" described in the claims.

Moreover, in the present embodiment, the engine control apparatus 9 and the processing of step S24 executed by the engine control apparatus 9 correspond to the "anomaly final determination unit" described in the claims, and the processing of step S24 corresponds to the "anomaly final determination step" described in the claims.

B. Second Embodiment

Figure 5:
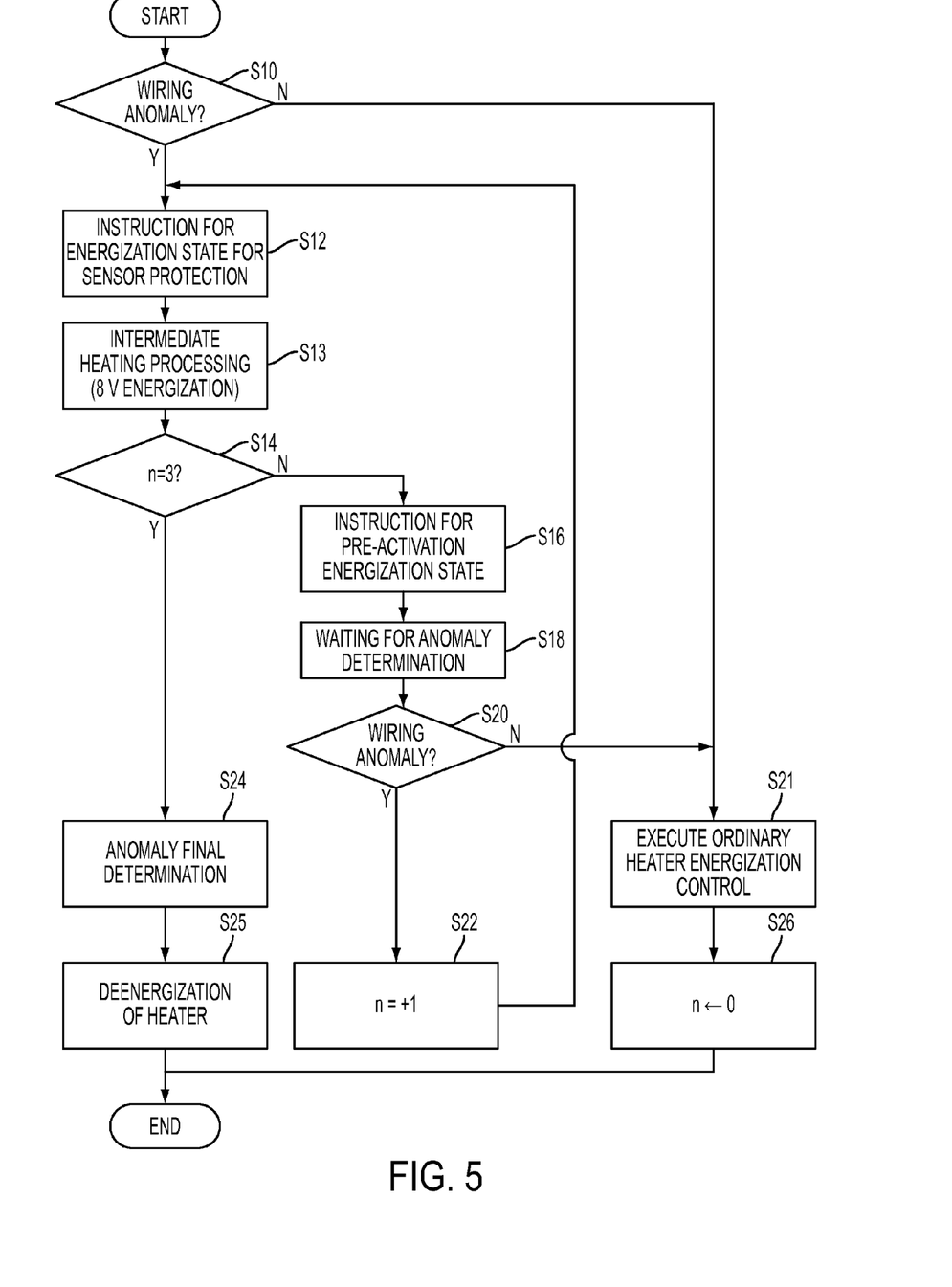
FIG. 5 Flowchart showing anomaly final determination processing according to a second embodiment.

FIG. 5 is a flowchart showing anomaly final determination processing according to a second embodiment of the present invention, which is executed in an internal-combustion-engine control system including a gas sensor control apparatus. The internal-combustion-engine control system according to the second embodiment differs from the internal-combustion-engine control system 1 of the first embodiment in the details of the anomaly final determination processing, and is identical with the internal-combustion-engine control system 1 of the first embodiment in the remaining software configuration and the hardware configuration. This anomaly final determination processing corresponds to the anomaly final determination processing of the first embodiment shown in FIG. 4, but additionally includes processing for energization control of the heater 43 by the heater control circuit 60.

As in the case of the first embodiment, the anomaly final determination processing according to the second embodiment is executed in the engine control apparatus 9 as a sub-routine separately from the sensor energization control processing, which is executed as the main routine. Notably, separately from the anomaly final determination processing, the engine control apparatus 9 executes the following ordinary control processing for the energization control of the heater 43 by the heater control circuit 60. When the sensor element 10 is not in an activated state, the ordinary control processing causes the heater control circuit 60 to energize the heater 43 at the maximum voltage (in the present embodiment, the battery voltage of 12 V). Meanwhile, when the sensor element 10 is in the activated state, on the basis of the separately detected element resistance signal of the gas sensor, the ordinary control processing causes the heater control circuit 60 to control, through PWM control, the voltage supplied to the heater 43 such that the element resistance of the sensor element 10 becomes equal to a target element resistance. Notably, since a method of controlling the voltage supplied to the heater 43 on the basis of the element resistance signal is known from, for example, Japanese Patent Application Laid-Open (kokai) No. H10-48180, the method will not be described further.

When the anomaly final determination processing of the second embodiment is started, steps S10 and S12 identical with those of the first embodiment are executed. When an affirmative determination is made in step S10 (step S10: YES), after completion of the processing of step S12, the engine control apparatus 9 proceeds to step S13. In this S13, the engine control apparatus 9 stops the above-described ordinary control processing which is performed by use of the heater control circuit 60, and performs intermediate heating processing for causing the heater control circuit 60 to energize the heater 43 at an intermediate voltage (in the present embodiment, 8 V), which is lower than the maximum voltage but equal to or higher than a voltage at which the activation temperature of the sensor element 10 can be maintained. This intermediate heating processing detects the voltage of the battery power supply, and causes the heater control circuit 60 to control, through PWM control, the voltage supplied to the heater 43 such that the intermediate voltage (in the present embodiment, 8 V) is applied to the heater 43. As a result of execution of such intermediate heating processing, even when a wiring anomaly disappears later on, the temperature of the sensor element 10 is not increased excessively. Further, cooling of the sensor element 10 is suppressed. Therefore, it becomes possible to cause the sensor element 10 to return to the ordinary state without damaging it.

After completion of the processing of step S13, the engine control apparatus 9 executes the processing of step S14, which is identical with the processing of step S14 in the first embodiment. When a denial determination is made in step S14 (step S14: No), the engine control apparatus 9 executes the processing of steps S16, S18, and S20, which is identical with the processing of steps S16, S18, and S20 in the first embodiment. When a denial determination is made in step S20 (step S20: No), the engine control apparatus 9 proceeds to step S21. In this step S21, the engine control apparatus 9 executes the above-described ordinary control processing by use of the heater control circuit 60. If the engine control apparatus 9 is executing the ordinary control processing for the heater 43 at that time, the engine control apparatus 9 continues the ordinary control processing. Meanwhile, if the energization control of the heater 43 in step S13 or step S25 (to be described later) is being performed at that time, the engine control apparatus 9 stops the energization control, and executes the ordinary control processing again. After completion of the processing of step S21, the engine control apparatus 9 proceeds to step S26. After completion of the processing of step S26, which is identical with that of step S26 in the first embodiment, the engine control apparatus 9 waits until anomaly analysis processing is executed next time.

When an affirmative determination is made in step S20 (step S20: Yes), the engine control apparatus 9 proceeds to step S22. After completion of the processing of step S22, which is identical with that of step S22 in the first embodiment, the engine control apparatus 9 returns to step S12, and repeatedly executes the processing of the subsequent steps.

Meanwhile, an affirmative determination is made in step S14 (step S14: Yes), the engine control apparatus 9 proceeds to step S24, finally determines that an anomaly has occurred, and proceeds to step S25. In step S25, the engine control apparatus 9 executes the processing for deenergizing the heater 43. As a result, the heating by the heater 43 whose energization is controlled under the intermediate heating processing is stopped, whereby an excessive temperature increase of the sensor element 10 is prevented, and wasteful consumption of electrical power is suppressed.

Needless to say, the present invention is not limited to the above-described first and second embodiments, and encompasses various modifications and equivalents thereof which fall within the scope of the present invention. For example, although the sensor element 10 used in the embodiments is a wide-range air-fuel-ratio sensor, the present invention can be applied to an $NO_x$ sensor which includes a sensor element obtained by adding another cell to the above-described sensor element 10 and providing two measurement chambers therein.

However, in the case of such an $NO_x$ sensor, a single microcomputer (controller) collectively performs various controls of the gas sensor. Therefore, the instruction means, the setting means, and the wiring anomaly detection means are realized on the single controller. Further, the controller corresponds to the gas sensor control apparatus.

In the above-described second embodiment, when it is finally determined in step S24 that an anomaly has occurred, the processing for deenergizing the heater 43 is executed. However, the second embodiment may be modified such that, even after it is finally determined in step S24 that an anomaly has occurred, rather than deenergizing the heater 43, the energization of the heater 43 is continued by means of maintaining the intermediate heating processing.

DESCRIPTION OF REFERENCE NUMERALS

1: internal-combustion-engine control system
2: sensor control circuit
5: gas sensor control apparatus (electronic control unit)
8: gas sensor
9: engine control apparatus
10: sensor element
13, 23: solid electrolyte bodies
14, 24: cells (oxygen pump cell, oxygen-concentration detection cell)
12, 16: paired electrodes (first pump electrode, second pump electrode)
22, 28: paired electrodes (first detection electrode, second detection electrode)
43: heater
52: sensor drive circuit
55: control section
58: anomaly detection circuit
60: heater control circuit

The invention claimed is:

1. A gas sensor control apparatus including a sensor drive circuit which is connected to a gas sensor having at least one cell composed of a solid electrolyte body and a pair of electrodes provided on the solid electrolyte body and which is adapted to supply electricity to the cell in order to drive the gas sensor, the gas sensor control apparatus comprising:
a controller programmed to:
selectively output a deenergization instruction for setting the sensor drive circuit to a deenergization state for stopping supply of electricity to the cell and an energization instruction for setting the sensor drive circuit to an energization state for supplying electricity to the cell;
set the sensor drive circuit to the deenergized state or the energization state in accordance with the selectively output deenergization instruction or energization instruction, respectively;
detect a wiring anomaly of the sensor drive circuit or the gas sensor;
perform in response to detecting the wiring anomaly, return-from-anomaly checking processing so as to output the deenergization instruction for setting the sensor drive circuit to the deenergization state and then output the energization instruction for setting the sensor drive circuit to the energization state, and perform determination processing so as to determine whether or not the wiring anomaly has disappeared as a result of performance of the return-from-anomaly checking processing;
finally determine, on the basis of the result of the determination processing, whether or not the wiring anomaly has occurred; and
control a heater provided on the gas sensor so as to heat the cell to an activation temperature or higher, wherein the control comprises energizing the heater at an intermediate voltage which is lower than a maximum voltage, but not lower than a voltage at which the heater can maintain the activation temperature of the cell, during a period between a point in time at which the wiring anomaly is first detected and a point in time at which it is finally determined whether or not the wiring anomaly has occurred.

2. A gas sensor control apparatus according to claim 1, wherein, in response to determining that the wiring anomaly has not yet disappeared, the controller is further programmed to:
repeat the return-from-anomaly checking processing at least one more time, and finally determine that the wiring anomaly has occurred, when the wiring anomaly does not disappear even after the return-from-anomaly checking processing is performed a predetermined number of times equal to or greater than two times.

3. A gas sensor control apparatus according to claim 1, wherein the controller is further programmed to:
deenergize the heater when it is finally determined that the wiring anomaly has occurred.

4. A method of controlling a gas sensor control apparatus including a (i) sensor drive circuit which is connected to a gas sensor having at least one cell composed of a solid electrolyte body and a pair of electrodes provided on the solid electrolyte body and which is adapted to supply electricity to the cell in order to drive the gas sensor and (ii) a heater control circuit for controlling a heater provided on the gas sensor so as to heat the cell to an activation temperature or higher, wherein the sensor drive circuit is configured such that, in response to an externally applied deenergization instruction, the sensor drive circuit enters a deenergization state for stopping supply of electricity to the cell and, in response to an externally applied energization instruction, the sensor drive circuit enters an energization state for supplying electricity to the cell, the method comprising:
a wiring anomaly detection step of detecting a wiring anomaly of the sensor drive circuit or the gas sensor;
a determination step of performing, when the wiring anomaly is detected, return-from-anomaly checking processing so as to output to the sensor drive circuit the deenergization instruction for setting the sensor drive circuit to the deenergization state and then output to the sensor drive circuit the energization instruction for setting the sensor drive circuit to the energization state, and performing determination processing so as to determine whether or not the wiring anomaly has disappeared as a result of performance of the return-from-anomaly checking processing;
an anomaly final determination step of finally determining, on the basis of the result of the determination processing, whether or not the wiring anomaly has occurred; and
a step of controlling the heater control circuit such that the heater control circuit energizes the heater at an intermediate voltage which is lower than a maximum voltage but not lower than a voltage at which the heater can maintain the activation temperature of the cell, during a period between a point in time at which the wiring anomaly detection step first detects the wiring anomaly and a point in time at which the anomaly final determination step finally determines whether or not the wiring anomaly has occurred.

5. A gas sensor control method according to claim 4, wherein, when the determination processing determines that the wiring anomaly has not yet disappeared, the anomaly final determination step causes the return-from-anomaly checking processing of the determination step to be repeated at least one more time, and finally determines that the wiring anomaly has occurred, when the wiring anomaly does not disappear even after the return-from-anomaly checking processing is performed a predetermined number of times equal to or greater than two times.

6. A gas sensor control method according to claim 4, further comprising a step of controlling the heater control circuit such that the heater control circuit deenergizes the heater when the anomaly final determination step finally determines that the wiring anomaly has occurred.

* * * * *